United States Patent
Rosinko

(10) Patent No.: US 9,737,656 B2
(45) Date of Patent: Aug. 22, 2017

(54) INTEGRATION OF INFUSION PUMP WITH REMOTE ELECTRONIC DEVICE

(71) Applicant: Tandem Diabetes Care, Inc., San Diego, CA (US)

(72) Inventor: Michael Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 292 days.

(21) Appl. No.: 14/583,274

(22) Filed: Dec. 26, 2014

(65) Prior Publication Data

US 2015/0182695 A1  Jul. 2, 2015

Related U.S. Application Data

(60) Provisional application No. 61/920,932, filed on Dec. 26, 2013, provisional application No. 61/920,914, (Continued)

(51) Int. Cl.
 *A61M 31/00* (2006.01)
 *A61M 5/142* (2006.01)
 (Continued)

(52) U.S. Cl.
 CPC ........ *A61M 5/14244* (2013.01); *A61M 5/168* (2013.01); *G06F 19/3468* (2013.01);
 (Continued)

(58) Field of Classification Search
 CPC .... A61M 2005/14208; A61M 2205/18; A61M 2205/35; A61M 2205/3584;
 (Continued)

(56) References Cited

U.S. PATENT DOCUMENTS

| | | |
|---|---|---|
| 5,078,683 A | 1/1992 | Sancoff et al. |
| 5,429,602 A | 7/1995 | Hauser |

(Continued)

FOREIGN PATENT DOCUMENTS

| | | |
|---|---|---|
| EP | 1102194 A2 | 5/2001 |
| KR | 20090085114 A | 8/2009 |

(Continued)

OTHER PUBLICATIONS

Stapel, "Converting Between Decimals, Fractions, and Percents", 2006. http://www.purplemath.com/modules/percents2.htm.
(Continued)

*Primary Examiner* — Jason Flick
(74) *Attorney, Agent, or Firm* — Patterson Thuente Pedersen, P.A.

(57) ABSTRACT

A system and method can provide for a remote electronic device to be used to remotely initiate delivery of a medicament bolus with a medical device, such as an insulin pump, with the medical device providing audible or tactile confirmation of the programmed bolus. The bolus amount can be calculated by or programmed or otherwise entered into the smartphone, etc., and then transmitted to the medical device. When the pump receives the transmitted bolus amount, it issues one or more indications such as audible sounds and/or vibrations in any number of desired combinations. For instance, each individual sound or vibration may correspond to an increment of the medicament. The user can therefore determine the size of the medicament bolus by the number of sounds or vibrations and can confirm or cancel delivery of the bolus.

20 Claims, 12 Drawing Sheets

Related U.S. Application Data filed on Dec. 26, 2013, provisional application No. 61/920,902, filed on Dec. 26, 2013.

(51) Int. Cl.
*A61M 5/168* (2006.01)
*G06F 19/00* (2011.01)

(52) U.S. Cl.
CPC ............. *A61M 2005/14208* (2013.01); *A61M 2205/18* (2013.01); *A61M 2205/35* (2013.01); *A61M 2205/3584* (2013.01); *A61M 2205/3592* (2013.01); *A61M 2205/50* (2013.01)

(58) Field of Classification Search
CPC ...... A61M 2205/3592; A61M 2205/50; A61M 5/14244; A61M 5/168; G06F 19/3468
USPC ........................................................ 604/500
See application file for complete search history.

(56) References Cited

U.S. PATENT DOCUMENTS

| | | | |
|---|---|---|---|
| 5,497,772 A | 3/1996 | Schulman et al. |
| 5,582,593 A | 12/1996 | Hultman |
| 5,660,163 A | 8/1997 | Schulman et al. |
| 5,685,844 A | 11/1997 | Marttila |
| 5,713,856 A | 2/1998 | Eggers et al. |
| 5,719,761 A | 2/1998 | Gatti et al. |
| 5,759,199 A | 6/1998 | Snell et al. |
| 5,814,015 A | 9/1998 | Gargano et al. |
| 5,876,370 A | 3/1999 | Blomquist |
| 5,935,099 A | 8/1999 | Peterson et al. |
| 5,997,475 A | 12/1999 | Bortz |
| 6,070,761 A | 6/2000 | Bloom et al. |
| 6,241,704 B1 | 6/2001 | Peterson et al. |
| 6,379,301 B1 | 4/2002 | Worthington et al. |
| 6,427,088 B1 | 7/2002 | Bowman, IV et al. |
| 6,442,433 B1 | 8/2002 | Linberg |
| 6,468,242 B1 | 10/2002 | Wilson et al. |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,577,899 B2 | 6/2003 | Lebel et al. |
| 6,585,644 B2 | 7/2003 | Lebel et al. |
| 6,585,707 B2 | 7/2003 | Cabiri et al. |
| 6,589,229 B1 | 7/2003 | Connelly et al. |
| 6,599,281 B1 | 7/2003 | Struys et al. |
| 6,605,072 B2 | 8/2003 | Struys et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,694,191 B2 | 2/2004 | Starkweather et al. |
| 6,733,446 B2 | 5/2004 | Lebel et al. |
| 6,740,075 B2 | 5/2004 | Lebel et al. |
| 6,744,350 B2 | 6/2004 | Blomquist |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,772,331 B1 | 8/2004 | Hind et al. |
| 6,780,156 B2 | 8/2004 | Haueter et al. |
| 6,790,198 B1 | 9/2004 | White et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,821,484 B1 | 11/2004 | Gregersen |
| 6,852,104 B2 | 2/2005 | Blomquist |
| 6,872,200 B2 | 3/2005 | Mann et al. |
| 6,873,268 B2 | 3/2005 | Lebel et al. |
| 6,950,708 B2 | 9/2005 | Bowman IV et al. |
| 6,958,691 B1 | 10/2005 | Anderson et al. |
| 6,958,705 B2 | 10/2005 | Lebel et al. |
| 6,970,741 B1 | 11/2005 | Whitehurst et al. |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 7,024,245 B2 | 4/2006 | Lebel et al. |
| 7,092,796 B2 | 8/2006 | Vanderveen |
| 7,109,878 B2 | 9/2006 | Mann et al. |
| 7,156,808 B2 | 1/2007 | Quy |
| 7,171,274 B2 | 1/2007 | Starkweather et al. |
| 7,181,505 B2 | 2/2007 | Haller et al. |
| 7,256,888 B2 | 8/2007 | Staehr et al. |
| 7,278,983 B2 | 10/2007 | Ireland et al. |
| 7,341,577 B2 | 3/2008 | Gill |
| 7,347,819 B2 | 3/2008 | Lebel et al. |
| 7,347,836 B2 | 3/2008 | Peterson et al. |
| 7,356,382 B2 | 4/2008 | Vanderveen |
| 7,369,635 B2 | 5/2008 | Spital et al. |
| 7,440,806 B1 | 10/2008 | Whitehurst et al. |
| 7,471,994 B2 | 12/2008 | Ford et al. |
| 7,481,759 B2 | 1/2009 | Whitehurst et al. |
| 7,483,743 B2 | 1/2009 | Mann et al. |
| 7,493,171 B1 | 2/2009 | Whitehurst et al. |
| 7,497,827 B2 | 3/2009 | Brister et al. |
| 7,558,629 B2 | 7/2009 | Keimel et al. |
| 7,559,926 B1 | 7/2009 | Blischak |
| 7,651,845 B2 | 1/2010 | Doyle et al. |
| 7,654,976 B2 | 2/2010 | Peterson et al. |
| 7,668,731 B2 | 2/2010 | Martucci et al. |
| 7,678,071 B2 | 3/2010 | Lebel et al. |
| 7,711,402 B2 | 5/2010 | Shults et al. |
| 7,713,240 B2 | 5/2010 | Istoc et al. |
| 7,717,903 B2 | 5/2010 | Estes et al. |
| 7,737,581 B2 | 6/2010 | Spurlin et al. |
| 7,782,192 B2 | 8/2010 | Jeckelmann et al. |
| 7,801,596 B2 | 9/2010 | Fischell et al. |
| 7,806,886 B2 | 10/2010 | Kanderian et al. |
| 7,815,602 B2 | 10/2010 | Mann et al. |
| 7,815,622 B2 | 10/2010 | Istoc et al. |
| 7,819,843 B2 | 10/2010 | Mann et al. |
| 7,831,310 B2 | 11/2010 | Lebel et al. |
| 7,835,927 B2 | 11/2010 | Schlotterbeck et al. |
| 7,875,022 B2 | 1/2011 | Wenger et al. |
| 7,901,394 B2 | 3/2011 | Ireland et al. |
| 7,931,613 B2 | 4/2011 | Haueter et al. |
| 7,942,844 B2 | 5/2011 | Moberg et al. |
| 7,959,598 B2 | 6/2011 | Estes |
| 7,972,296 B2 | 7/2011 | Braig et al. |
| 7,979,136 B2 | 7/2011 | Young et al. |
| 7,983,745 B2 | 7/2011 | Hatlestad et al. |
| 7,999,674 B2 | 8/2011 | Kamen |
| 8,002,700 B2 | 8/2011 | Ferek-Petric et al. |
| 8,005,688 B2 | 8/2011 | Coffman et al. |
| 8,020,564 B2 | 9/2011 | Batch |
| 8,021,299 B2 | 9/2011 | Miesel et al. |
| 8,065,161 B2 | 11/2011 | Howard et al. |
| 8,095,123 B2 | 1/2012 | Gray |
| 8,099,074 B2 | 1/2012 | Ebner et al. |
| 8,106,534 B2 | 1/2012 | Spurlin et al. |
| 8,109,921 B2 | 2/2012 | Estes et al. |
| 8,117,481 B2 | 2/2012 | Anselmi et al. |
| 8,118,770 B2 | 2/2012 | Galley et al. |
| 8,121,689 B2 | 2/2012 | Kalgren et al. |
| 8,133,197 B2 | 3/2012 | Blomquist et al. |
| 8,152,764 B2 | 4/2012 | Istoc et al. |
| 8,152,789 B2 | 4/2012 | Starkweather et al. |
| 8,170,721 B2 | 5/2012 | Nickerson |
| 8,182,462 B2 | 5/2012 | Istoc et al. |
| 8,192,394 B2 | 6/2012 | Estes et al. |
| 8,192,395 B2 | 6/2012 | Estes et al. |
| 8,202,267 B2 | 6/2012 | Field et al. |
| 8,206,350 B2 | 6/2012 | Mann et al. |
| 8,206,378 B1 | 6/2012 | Kalpin et al. |

(56) References Cited

U.S. PATENT DOCUMENTS

| | | |
|---|---|---|
| 8,226,891 B2 | 7/2012 | Sloan et al. |
| 8,231,562 B2 | 7/2012 | Buck et al. |
| 8,234,128 B2 | 7/2012 | Martucci et al. |
| 8,250,483 B2 | 8/2012 | Blomquist |
| 8,257,300 B2 | 9/2012 | Budiman et al. |
| 8,269,634 B2 | 9/2012 | Fischell et al. |
| 8,285,328 B2 | 10/2012 | Caffey et al. |
| 8,287,487 B2 | 10/2012 | Estes |
| 8,287,495 B2 | 10/2012 | Michaud et al. |
| 8,294,581 B2 | 10/2012 | Kamen |
| 8,298,184 B2 | 10/2012 | Diperna et al. |
| 8,308,680 B1 | 11/2012 | Chawla |
| 8,311,749 B2 | 11/2012 | Brauker et al. |
| 8,323,188 B2 | 12/2012 | Tran |
| 8,344,847 B2 | 1/2013 | Moberg et al. |
| 8,346,399 B2 | 1/2013 | Blomquist |
| 8,348,885 B2 | 1/2013 | Moberg et al. |
| 8,376,943 B2 | 2/2013 | Kovach et al. |
| 8,380,536 B2 | 2/2013 | Howard et al. |
| 8,395,581 B2 | 3/2013 | Gråskov et al. |
| 8,414,523 B2 | 4/2013 | Blomquist et al. |
| 8,414,557 B2 | 4/2013 | Istoc et al. |
| 8,444,595 B2 | 5/2013 | Brukalo et al. |
| 8,449,523 B2 | 5/2013 | Brukalo et al. |
| 8,451,230 B2 | 5/2013 | Celentano et al. |
| 8,452,413 B2 | 5/2013 | Young et al. |
| 8,454,554 B2 | 6/2013 | Reinke et al. |
| 8,456,301 B2 | 6/2013 | Fennell et al. |
| 8,469,920 B2 | 6/2013 | Mernoe et al. |
| 8,472,913 B2 | 6/2013 | Ebner et al. |
| 8,491,566 B2 | 7/2013 | Ramey et al. |
| 8,502,662 B2 | 8/2013 | Pohlman et al. |
| 8,517,987 B2 | 8/2013 | Istoc et al. |
| 8,533,475 B2 | 9/2013 | Frikart et al. |
| 8,545,483 B2 | 10/2013 | Schwabe et al. |
| 8,562,590 B2 | 10/2013 | Yodfat et al. |
| 8,568,357 B2 | 10/2013 | Ortega et al. |
| 8,573,027 B2 | 11/2013 | Rosinko et al. |
| 8,601,465 B2 | 12/2013 | Bernstein et al. |
| 8,641,671 B2 | 2/2014 | Michaud et al. |
| 8,710,993 B2 | 4/2014 | Hayter et al. |
| 8,768,717 B2 | 7/2014 | Blomquist |
| 8,801,655 B2 | 8/2014 | Mernoe et al. |
| 8,868,794 B2 | 10/2014 | Masoud et al. |
| 8,903,350 B2 | 12/2014 | Ebner et al. |
| 8,932,250 B2 | 1/2015 | Montgomery |
| 8,936,565 B2 | 1/2015 | Chawla |
| 8,938,306 B2 | 1/2015 | Lebel et al. |
| 8,977,883 B2 | 3/2015 | Imhof et al. |
| 8,986,253 B2 | 3/2015 | DiPerna |
| 8,992,475 B2 | 3/2015 | Mann et al. |
| 9,049,982 B2 | 6/2015 | Brukalo et al. |
| 9,065,720 B2 | 6/2015 | Allen et al. |
| 9,101,714 B2 | 8/2015 | Miyazaki et al. |
| 9,114,210 B2 | 8/2015 | Estes |
| 9,132,227 B2 | 9/2015 | Bryant, Jr. et al. |
| 9,143,941 B2 | 9/2015 | Wang et al. |
| 9,173,992 B2 | 11/2015 | Bengtsson et al. |
| 9,259,531 B2 | 2/2016 | Kamen et al. |
| 9,308,319 B2 | 4/2016 | Mernoe et al. |
| 2001/0041869 A1 | 11/2001 | Causey et al. |
| 2002/0029776 A1 | 3/2002 | Blomquist |
| 2002/0065454 A1 | 5/2002 | Lebel et al. |
| 2002/0128594 A1 | 9/2002 | Das et al. |
| 2002/0193679 A1 | 12/2002 | Malave et al. |
| 2003/0028089 A1 | 2/2003 | Galley et al. |
| 2003/0055570 A1 | 3/2003 | Ribeiro, Jr. |
| 2003/0060765 A1 | 3/2003 | Campbell et al. |
| 2003/0065308 A1 | 4/2003 | Lebel et al. |
| 2003/0130616 A1 | 7/2003 | Steil et al. |
| 2003/0163223 A1 | 8/2003 | Blomquist |
| 2003/0208113 A1 | 11/2003 | Mault et al. |
| 2004/0068230 A1* | 4/2004 | Estes ............... A61B 5/0002 604/154 |
| 2004/0073095 A1 | 4/2004 | Causey et al. |
| 2004/0122353 A1 | 6/2004 | Shahmirian et al. |
| 2004/0193090 A1 | 9/2004 | Lebel et al. |
| 2004/0235446 A1 | 11/2004 | Flaherty et al. |
| 2005/0021006 A1 | 1/2005 | Tonnies |
| 2005/0060030 A1 | 3/2005 | Lashinski et al. |
| 2005/0065464 A1 | 3/2005 | Talbot et al. |
| 2005/0137530 A1 | 6/2005 | Campbell et al. |
| 2005/0143864 A1 | 6/2005 | Blomquist |
| 2005/0177395 A1 | 8/2005 | Blomquist |
| 2005/0246416 A1 | 11/2005 | Blomquist |
| 2006/0031094 A1 | 2/2006 | Cohen et al. |
| 2006/0173444 A1 | 8/2006 | Choy et al. |
| 2006/0253296 A1 | 11/2006 | Liisberg et al. |
| 2007/0016170 A1 | 1/2007 | Kovelman |
| 2007/0016449 A1 | 1/2007 | Cohen et al. |
| 2007/0033074 A1 | 2/2007 | Nitzan et al. |
| 2007/0060869 A1 | 3/2007 | Tolle et al. |
| 2007/0060870 A1 | 3/2007 | Tolle et al. |
| 2007/0093786 A1 | 4/2007 | Goldsmith et al. |
| 2007/0156033 A1 | 7/2007 | Causey, III et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2008/0033357 A1 | 2/2008 | Mann et al. |
| 2008/0033361 A1 | 2/2008 | Evans et al. |
| 2008/0065007 A1 | 3/2008 | Peterson et al. |
| 2008/0065016 A1 | 3/2008 | Peterson et al. |
| 2008/0071251 A1 | 3/2008 | Moubayed et al. |
| 2008/0071580 A1 | 3/2008 | Marcus et al. |
| 2008/0076969 A1 | 3/2008 | Kraft et al. |
| 2008/0126969 A1 | 5/2008 | Blomquist |
| 2008/0139910 A1 | 6/2008 | Mastrototaro et al. |
| 2008/0147050 A1 | 6/2008 | Mann et al. |
| 2008/0172026 A1 | 7/2008 | Blomquist et al. |
| 2008/0183060 A1 | 7/2008 | Steil et al. |
| 2008/0287922 A1 | 11/2008 | Panduro |
| 2008/0300651 A1 | 12/2008 | Gerber et al. |
| 2008/0312584 A1 | 12/2008 | Montgomery |
| 2009/0005726 A1 | 1/2009 | Jones et al. |
| 2009/0018495 A1 | 1/2009 | Panduro |
| 2009/0018779 A1 | 1/2009 | Cohen et al. |
| 2009/0024178 A1 | 1/2009 | Hennig |
| 2009/0030382 A1 | 1/2009 | Brandt et al. |
| 2009/0030398 A1 | 1/2009 | Yodfat et al. |
| 2009/0030733 A1 | 1/2009 | Cohen et al. |
| 2009/0036753 A1 | 2/2009 | King |
| 2009/0043290 A1 | 2/2009 | Villegas et al. |
| 2009/0085768 A1 | 4/2009 | Patel et al. |
| 2009/0088731 A1 | 4/2009 | Campbell et al. |
| 2009/0131861 A1 | 5/2009 | Braig et al. |
| 2009/0150186 A1 | 6/2009 | Cohen et al. |
| 2009/0163855 A1 | 6/2009 | Shin et al. |
| 2009/0177142 A1 | 7/2009 | Blomquist et al. |
| 2009/0212966 A1 | 8/2009 | Panduro |
| 2009/0227855 A1 | 9/2009 | Hill et al. |
| 2009/0240193 A1 | 9/2009 | Mensinger et al. |
| 2009/0270833 A1 | 10/2009 | DeBelser et al. |
| 2009/0275886 A1 | 11/2009 | Blomquist et al. |
| 2010/0069890 A1 | 3/2010 | Gråskov et al. |
| 2010/0094251 A1 | 4/2010 | Estes |
| 2010/0121415 A1 | 5/2010 | Skelton et al. |
| 2010/0130933 A1 | 5/2010 | Holland et al. |
| 2010/0156633 A1 | 6/2010 | Buck et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0174230 A1 | 7/2010 | Istoc et al. |
| 2010/0174553 A1 | 7/2010 | Kaufman et al. |
| 2010/0198142 A1 | 8/2010 | Sloan et al. |
| 2010/0198143 A1 | 8/2010 | Estes et al. |
| 2010/0198520 A1 | 8/2010 | Breton et al. |
| 2010/0205001 A1 | 8/2010 | Knudsen et al. |
| 2010/0218132 A1 | 8/2010 | Soni et al. |

(56) References Cited

U.S. PATENT DOCUMENTS

| | | |
|---|---|---|
| 2010/0249530 A1 | 9/2010 | Rankers et al. |
| 2010/0262117 A1 | 10/2010 | Magni et al. |
| 2010/0274592 A1 | 10/2010 | Nitzan et al. |
| 2010/0280329 A1 | 11/2010 | Randløv et al. |
| 2010/0280442 A1 | 11/2010 | Shahmirian et al. |
| 2010/0295686 A1 | 11/2010 | Sloan et al. |
| 2010/0298662 A1 | 11/2010 | Yu et al. |
| 2010/0298685 A1 | 11/2010 | Hayter et al. |
| 2010/0331651 A1 | 12/2010 | Groll |
| 2011/0004275 A1 | 1/2011 | Carbunaru et al. |
| 2011/0009846 A1 | 1/2011 | Istoc et al. |
| 2011/0040247 A1* | 2/2011 | Mandro ............ A61M 5/142 604/66 |
| 2011/0040251 A1 | 2/2011 | Blomquist et al. |
| 2011/0046697 A1 | 2/2011 | Gerber et al. |
| 2011/0050428 A1 | 3/2011 | Istoc |
| 2011/0071372 A1 | 3/2011 | Sloan et al. |
| 2011/0071765 A1 | 3/2011 | Yodfat et al. |
| 2011/0077493 A1 | 3/2011 | Shadforth et al. |
| 2011/0077963 A1 | 3/2011 | Knudsen et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0118699 A1 | 5/2011 | Yodfat et al. |
| 2011/0124996 A1 | 5/2011 | Reinke et al. |
| 2011/0125095 A1 | 5/2011 | Lebel et al. |
| 2011/0126188 A1 | 5/2011 | Bernstein et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0166544 A1 | 7/2011 | Verhoef et al. |
| 2011/0172744 A1 | 7/2011 | Davis et al. |
| 2011/0178462 A1 | 7/2011 | Moberg et al. |
| 2011/0184653 A1 | 7/2011 | Ray et al. |
| 2011/0190694 A1 | 8/2011 | Lanier, Jr. et al. |
| 2011/0205065 A1 | 8/2011 | Strachan et al. |
| 2011/0208155 A1 | 8/2011 | Palerm et al. |
| 2011/0213225 A1 | 9/2011 | Bernstein et al. |
| 2011/0230837 A1 | 9/2011 | Kamen et al. |
| 2011/0256024 A1 | 10/2011 | Cole et al. |
| 2011/0275410 A1 | 11/2011 | Caffey et al. |
| 2012/0013625 A1 | 1/2012 | Blomquist et al. |
| 2012/0013802 A1 | 1/2012 | Blomquist et al. |
| 2012/0016295 A1 | 1/2012 | Tsoukalis |
| 2012/0029433 A1 | 2/2012 | Michaud et al. |
| 2012/0030610 A1 | 2/2012 | Diperna et al. |
| 2012/0041415 A1 | 2/2012 | Estes et al. |
| 2012/0059673 A1 | 3/2012 | Cohen et al. |
| 2012/0091813 A1 | 4/2012 | Spurlin et al. |
| 2012/0191061 A1 | 7/2012 | Yodfat et al. |
| 2012/0191063 A1 | 7/2012 | Brauker et al. |
| 2012/0220939 A1 | 8/2012 | Yodfat et al. |
| 2012/0232520 A1 | 9/2012 | Sloan et al. |
| 2012/0302991 A1 | 11/2012 | Blomquist et al. |
| 2012/0330227 A1 | 12/2012 | Budiman et al. |
| 2013/0012878 A1 | 1/2013 | Blomquist |
| 2013/0015980 A1 | 1/2013 | Evans et al. |
| 2013/0018315 A1 | 1/2013 | Blomquist |
| 2013/0053816 A1 | 2/2013 | DiPerna et al. |
| 2013/0123745 A1 | 5/2013 | Simmons |
| 2013/0131630 A1 | 5/2013 | Blomquist |
| 2013/0159456 A1 | 6/2013 | Daoud et al. |
| 2013/0324928 A1 | 12/2013 | Kruse |
| 2013/0331790 A1 | 12/2013 | Brown et al. |
| 2014/0054883 A1 | 2/2014 | Lanigan et al. |
| 2014/0094744 A1 | 4/2014 | Blomquist |
| 2014/0094764 A1 | 4/2014 | Blomquist |
| 2014/0095485 A1 | 4/2014 | Blomquist |
| 2014/0095499 A1 | 4/2014 | Blomquist |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276574 A1 | 9/2014 | Saint |
| 2014/0323961 A1 | 10/2014 | Blomquist et al. |
| 2015/0072613 A1 | 3/2015 | Swanson |
| 2015/0182693 A1 | 7/2015 | Rosinko |
| 2015/0182694 A1 | 7/2015 | Rosinko |
| 2015/0217044 A1 | 8/2015 | Blomquist |
| 2015/0314062 A1 | 11/2015 | Blomquist et al. |
| 2015/0320933 A1 | 11/2015 | Estes |
| 2015/0352282 A1 | 12/2015 | Mazlish |
| 2016/0082188 A1 | 3/2016 | Blomquist et al. |
| 2016/0271325 A1 | 9/2016 | Farnan et al. |

FOREIGN PATENT DOCUMENTS

| | | |
|---|---|---|
| WO | WO 2008127694 A1 | 10/2008 |
| WO | WO 2013184896 A1 | 12/2013 |

OTHER PUBLICATIONS

Application and File History for U.S. Appl. No. 13/730,164, filed Dec. 28, 2012, inventors Blomquist et al.

Search Report and Written Opinion dated Apr. 14, 2015 for PCT Application No. PCT/US2014/072181 filed Dec. 23, 2014, 11 pages.

Application and File history for U.S. Appl. No. 14/581,461, filed Dec. 23, 2014. Inventor: Rosinko.

Search Report and Written Opinion dated Apr. 24, 2015 for PCT Application No. PCT/US2014/072429 filed Dec. 26, 2014, 13 pages.

* cited by examiner

INTEGRATION OF INFUSION PUMP WITH REMOTE ELECTRONIC DEVICE

RELATED APPLICATIONS

The present application claims the benefit of U.S. Provisional Application No. 61/920,932 filed Dec. 26, 2013, U.S. Provisional Application No. 61/920,914 filed Dec. 26, 2013, and U.S. Provisional Application No. 61/920,902 filed Dec. 26, 2013, each of which is incorporated herein in its entirety by reference.

FIELD OF THE INVENTION

The present invention relates to wireless control of and/or communication with drug delivery devices.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of insulin-injecting pumps that have been developed for the administration of insulin for those suffering from both type I and type II diabetes. Some insulin injecting pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. patent application Ser. No. 13/838,617, U.S. patent application Ser. No. 13/827,707 and U.S. Pat. No. 8,287,495, each of which is hereby incorporated herein by reference in its entirety.

With the proliferation of handheld electronic devices, such as mobile phones (e.g., smartphones), there is a desire to be able to remotely utilize such devices to optimize usage of infusion pump devices.

Infusion pumps are often discretely located on or around a patient, such as beneath clothing or in a carrying pouch. Some infusion pumps are therefore adapted to be programmed and/or controlled with remote devices that enable programming and/or control without directly interacting with a user interface of the pump. These remote controllers therefore enable a pump to be programmed and/or operated more privately and comfortably. Accordingly, one potential use of such handheld consumer electronic devices, such as smartphones, tablets and the like, is to utilize such devices as a controller for remotely programming and/or operating an infusion pump. However, without viewing the pump there would be no way to determine whether the pump is, e.g., receiving commands from the smartphone, has been properly programmed by the smartphone, etc., and therefore the risk of improper medicament delivery could exist.

Many infusion pumps design to delivery insulin to a patient are capable of integrating with diabetes management software run on a computer. Such software typically provides a convenient and visual way to display data from the pump and associated devices, such as blood glucose meters. Use of such systems enables patients and caregivers to easily track and analyze treatment data and trends to optimize diabetes therapy. However, in many cases, data must be transferred from the pump directly to a computer running the management software by a wired connection or with a portable memory device such as a flash drive. Inconveniences posed by such requirements can lead to data not being timely or properly or ever transferred to the management software, which in turn leads to under or improper utilization of the software or in some cases the software not being used at all.

In addition, the typical age of diagnosis of type I diabetes is 14 years old or younger. Thus, a significant percentage of the people that utilize insulin pumps are children who may spend their time in, e.g., daycare facilities, school, or other locations away from parents or primary caregivers. Generally, children below a certain age are not given the responsibility of monitoring their blood sugar levels and/or dosing insulin themselves, and therefore when those children are at school they must obtain the assistance of an adult such as the school nurse, teacher, etc., each time insulin needs to be dosed. This frequently presents an inconvenience to both the child as well as to school officials, and even the child's peers, not to mention embarrassment for the child patient and disruption of the child's educational experience. It would therefore be desirable for children to safely play a larger role in the management of their disease by providing a way for them to initiate dosing of insulin and/or other medicaments themselves, while still providing some level of oversight from an adult, without the child having to personally visit a school nurse or other authorized caregiver.

SUMMARY OF THE INVENTION

Systems and methods according to embodiments of the present invention provide for use of devices such as a mobile telephone (sometimes referred to as a cellular telephone), such as a smartphone, or other computing device such as a tablet, laptop computer, personal computer, etc. to remotely program, control and/or communicate with an infusion pump.

A system and method can provide for a remote electronic device to be used to remotely initiate delivery of a medicament bolus with a medical device, such as an insulin pump, with the medical device providing audible or tactile confirmation of the programmed bolus. The bolus amount can be calculated by or programmed or otherwise entered into the smartphone, etc., and then transmitted to the medical device. When the pump receives the transmitted bolus amount, it issues one or more indications such as audible sounds and/or vibrations in any number of desired combinations. For instance, each individual sound or vibration may correspond to an increment of the medicament. The user can therefore determine the size of the medicament bolus by the number of sounds or vibrations and can confirm or cancel delivery of the bolus.

In one such embodiment, a smartphone communicates with an insulin pump to facilitate delivery and confirmation of an insulin bolus to a patient with the pump. The smartphone can include a software application and/or firmware that permit programming and/or calculation of an insulin bolus and transmission of a bolus command or communication to the pump. The pump receives the bolus command and provides audible and/or tactile feedback to the user indicating the size of the bolus. For example, each sound or vibration may, for example, correspond to 0.5 units of insulin to be delivered. Thus, if the pump provides ten beeps or vibrations, the user knows the pump is intending to deliver a bolus of five units of insulin based on the received command. If this is an expected and/or acceptable amount, the user can confirm the delivery to permit the pump to deliver the bolus.

A system and method can also provide for remote authorization of delivery of a medicament with a medical device, such as, an infusion pump is described. A caregiver device controlled by a parent or other caregiver, such as a smartphone, can be in wireless communication with a patient being treated with a medical device, such as a minor child. Information pertaining to a requested operation to be performed by the medical device can be transmitted from the medical device to the caregiver device. The caregiver can review information pertaining to the request on the caregiver device to determine if the operation should be performed. If the caregiver authorizes the operation, a confirmation can be send to the medical device and the operation is then performed.

In one such embodiment, a system for remote authorization of delivery of a medicament includes a caregiver device, such as a mobile phone (e.g., a smartphone), and a medical device, such as an insulin pump, in wireless communication with each other. A request for delivery of insulin with the insulin pump, such as delivery of a meal bolus, can be sent from the insulin pump to the caregiver smartphone. The caregiver can review the request and corresponding information and, if appropriate, authorize the request. Once the request is authorized, the insulin pump can proceed with delivery of the requested amount of insulin, either automatically or upon receiving patient confirmation.

In another such embodiment, a method for remotely authorizing delivery of a medicament by a medical device, such as an insulin pump, includes receiving a request for insulin delivery from the infusion pump at a caregiver device, such as a smartphone. The request as well as corresponding information, such as, for example, blood glucose level and insulin on board, can be reviewed on the caregiver device. Authorization to deliver insulin can be provided by the caregiver through the smartphone and transmitted to the insulin pump. The pump can then proceed with delivery of the requested amount of insulin.

A system and method can further provide for use of a mobile phone, such as a smartphone, to aid in determining, programming and data tracking therapy provided by a medical device such as an insulin pump. A smartphone can be in wireless communication with an insulin pump and can also be capable of connecting to one or more additional devices, such as a blood glucose meter or a therapy management system. The smartphone can facilitate the transfer of data and measurements between and among these devices.

In one such embodiment, a smartphone communicates with an insulin pump and a blood glucose meter. The smartphone can connect to the blood glucose meter to receive a current or recent blood glucose value and then transmit that value to the insulin pump. The pump can then use that recent value to determine whether a bolus is needed. A communication can then be sent to the phone to confirm to the user whether a bolus is or is not needed, and the user can refer to the pump to deliver a needed bolus.

In another such embodiment, a smartphone communicates with a therapy management system to enhance data logging relating to treatment with an insulin pump. Features of the smartphone such as the camera or speaker can obtain files, such as images or voice recordings, containing information on meals to be consumed by the user. These files can be transmitted to the therapy management system for incorporation into the data analysis of the system and correlated with therapy delivered by the pump that is also tracked by the system.

Certain embodiments are described further in the following description, examples, claims, and drawings. These embodiments will become more apparent from the following detailed description when taken in conjunction with the accompanying exemplary drawings.

DETAILED DESCRIPTION

Figure 1:
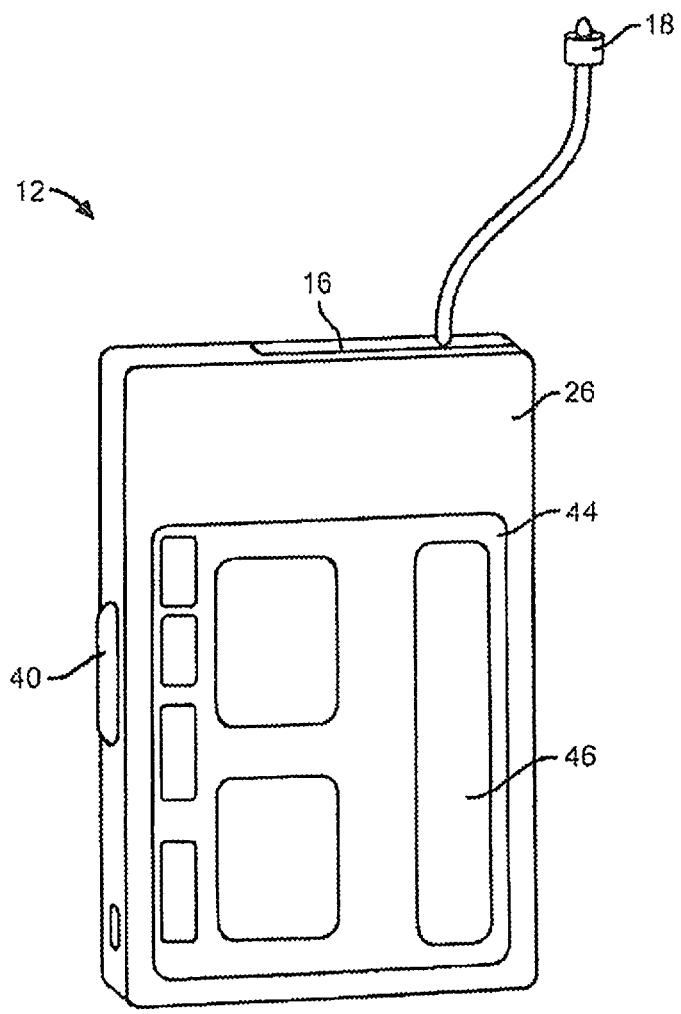
FIG. 1 is a medical device that can be utilized with embodiments of the present invention.

FIG. 1 depicts an embodiment of a medical device that can be used with embodiments of the present invention. In this embodiment, the medical device is configured as a pump 12 such as an infusion pump that can include a pumping or delivery mechanism and reservoir for delivering medicament to a patient and an output/display 44. The type of output/display 44 may vary as may be useful for a particular application. The type of visual output/display may include LCD displays, LED displays, plasma displays, graphene-based displays, OLED displays and the like. The output/display 44 may also be an interactive or touch sensitive screen 46 having an input device such as, for example, a touch screen comprising a capacitive screen or a resistive screen. The pump 12 may additionally include a keyboard or other input device known in the art for data entry, which may be separate from the display. The pump 12 may also include a capability to operatively couple to a secondary display device such as a remote display, a remote control device, a laptop computer, personal computer, tablet computer, mobile communication device such as a smartphone or personal digital assistant (PDA) or the like. In other embodiments, the pump 12 may not include a display.

In one embodiment, medical device can be a portable insulin pump configured to deliver insulin to a patient. Further details regarding such pump devices can be found in U.S. Pat. No. 8,641,671, which is incorporated herein by reference in its entirety. In other embodiments, medical device can be an infusion pump configured to deliver one or more additional or other medicaments to a patient. In a further embodiment, the medical device can be a glucose meter such as a continuous glucose monitor. Further detail regarding such systems and definitions of related terms can be found in, e.g., U.S. Pat. Nos. 8,311,749, 7,711,402 and 7,497,827, each of which is hereby incorporated by reference herein in its entirety. In other embodiments, the medical device can monitor other physiological parameters of a patient.

Figure 2:
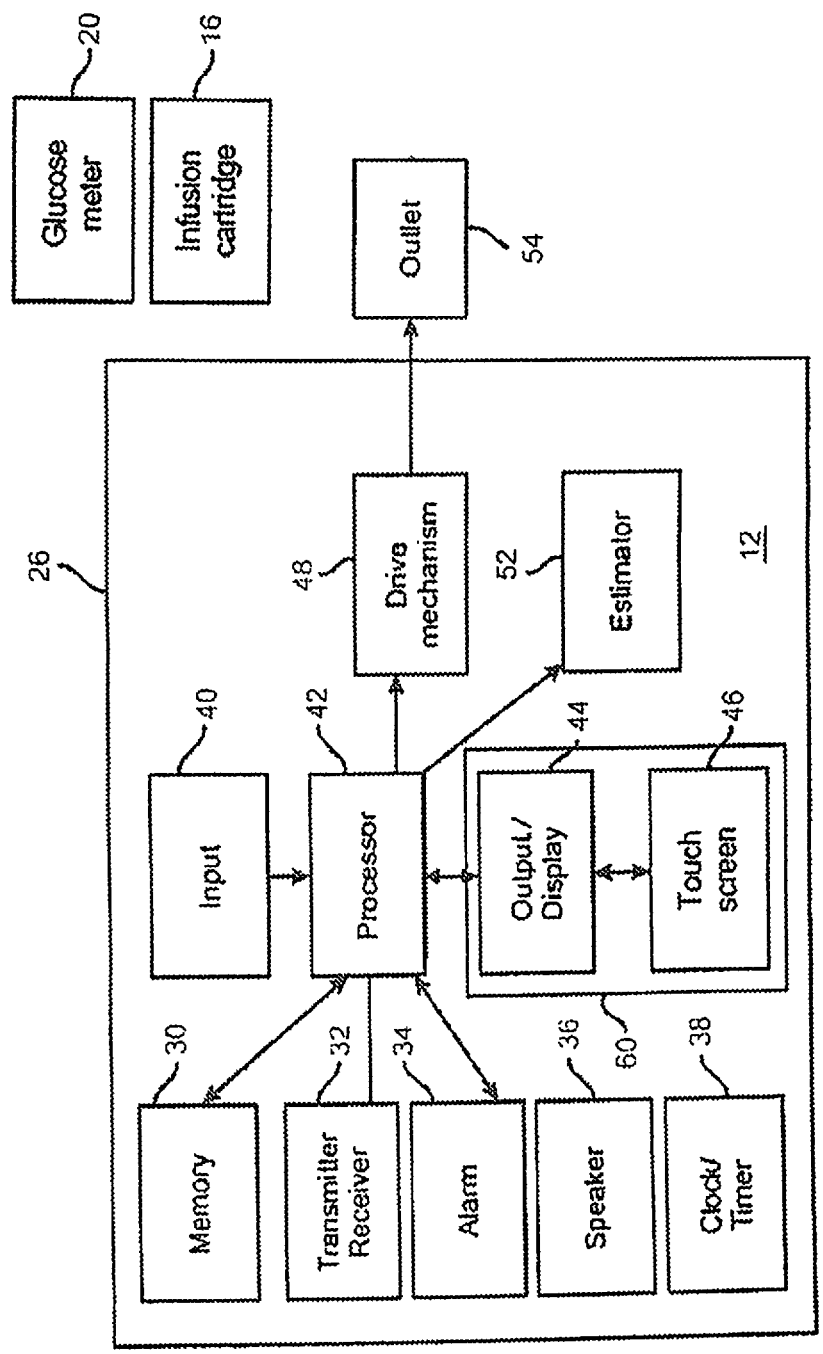
FIG. 2 is a block diagram representing a medical device that can be used with embodiments of the present invention.

FIG. 2 illustrates a block diagram of some of the features that may be incorporated within the housing 26 of a medical device such as a pump 12 that can be used with embodiments of the present invention. The pump 12 can include a processor 42 that controls the overall functions of the device. The infusion pump 12 may also include a memory device 30, a transmitter/receiver 32, an alarm 34, a speaker 36, a clock/timer 38, an input device 40, a user interface suitable for accepting input and commands from a user such as a caregiver or patient, a drive mechanism 48, and an estimator device 52. One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices; for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters. In some embodiments, the processor 42 can communicate with a safety processor as disclosed in U.S. patent application Ser. No. 14/581,461, entitled Safety Processor for Wireless Control of a Drug Delivery Device, which is hereby incorporated by reference herein in its entirety.

Figure 3:
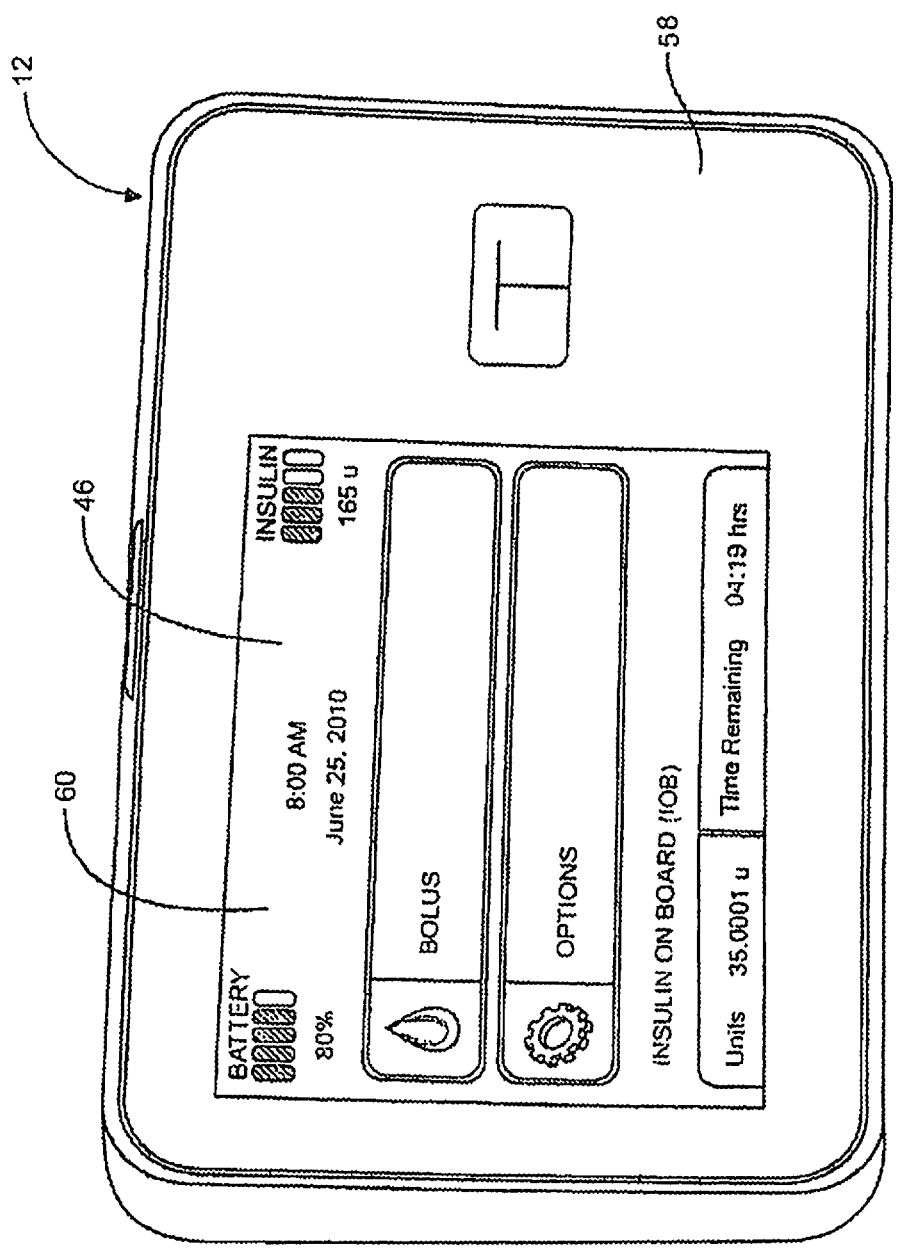
FIG. 3 depicts a medical device such as an insulin infusion pump that can be used with embodiments of the present invention displaying on a user interface an exemplary screen shot of a home page of the user interface.

Referring to FIG. 3, a front view of a pump 12 is depicted. Pump 12 may include a user interface, such as, for example, a GUI 60 on a front surface 58 or other location of pump 12. GUI 60 may include a touch-sensitive screen 46 that may be configured for displaying data, facilitating data and/or command entry, providing visual tutorials, as well as other interface features that may be useful to a caregiver or to the patient operating pump 12. The GUI can also present alarms or alerts to the user.

In some embodiments, pump 12 can be used to deliver a "quick" or "audio" bolus of medicament. A quick bolus enables programming of a bolus using a single button with the pump confirming the configuration of the bolus with audible sounds, vibrations, visual indications or combinations thereof. Depictions of various quick bolus delivery configuration pages 62 that can be displayed on the graphical user interface 60 of a pump 12 are depicted in FIGS. 4A-4D.

Figure 4:
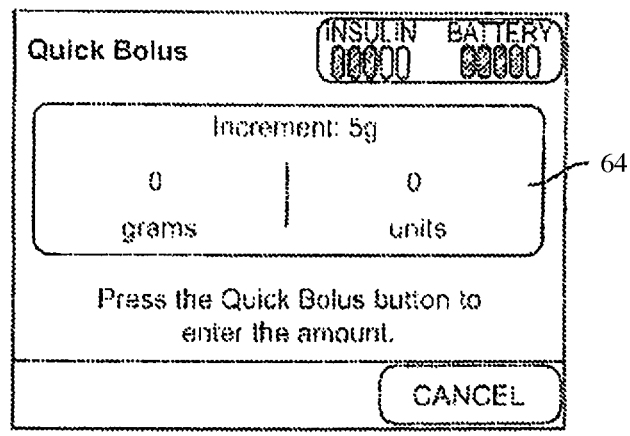
FIG. 4A is an exemplary screen shot of a "quick bolus" page of a user interface of a medical device such as an infusion pump according to an embodiment of the present invention.
FIG. 4B is an exemplary screen shot of a "quick bolus" page of a user interface of a medical device such as an infusion pump according to an embodiment of the present invention.
FIG. 4C is an exemplary screen shot of a "quick bolus" page of a user interface of a medical device such as an infusion pump according to an embodiment of the present invention.
FIG. 4D is an exemplary screen shot of a "quick bolus" page of a user interface of a medical device such as an infusion pump according to an embodiment of the present invention.
Figure 4:
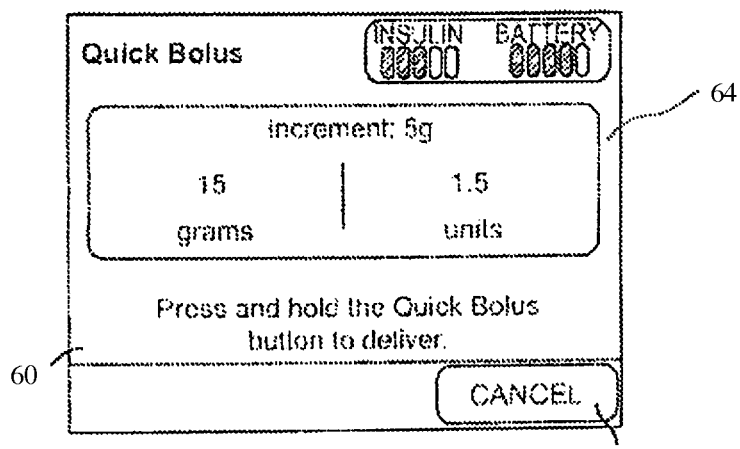
Figure 4:
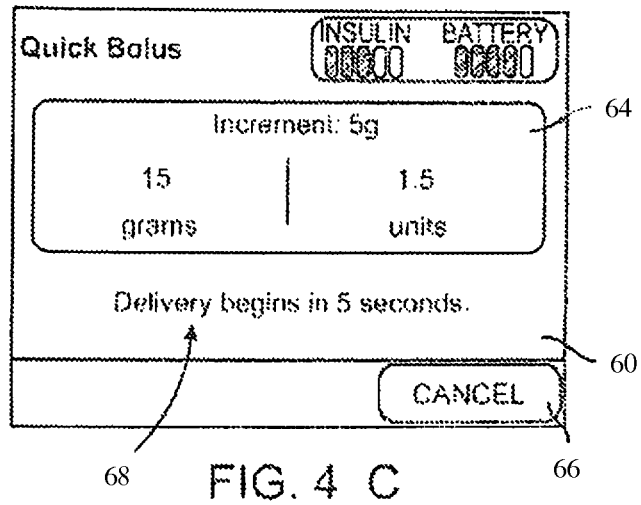
Figure 4:
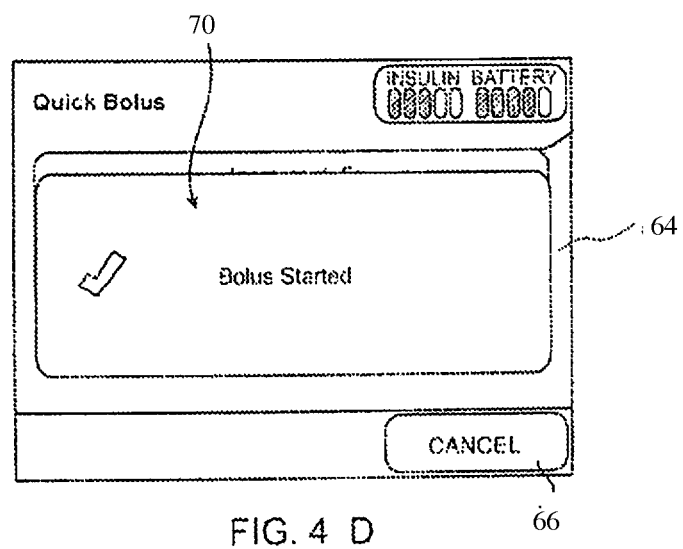

When a quick bolus option is activated or selected, a quick bolus delivery configuration page 64, such as shown in FIG. 4A, can be displayed on the user interface. The quick bolus delivery configuration page 64 asks the user to press a quick bolus button (which can be, for example, a physical button or switch on pump 12 or a touch-selectable portion of the user interface 60) one or more times to increase the size of a desired bolus. The bolus size can be increased, for example, based on a fixed number of carbohydrates associated with each button press and/or by a fixed number of units of insulin corresponding to each button press. Each time the user presses the bolus button, for example, the grams of carbohydrates and units of insulin displayed on the quick bolus delivery configuration page increases. For example, as shown in FIG. 4B, if the pump has stored a predefined value of five grams of carbohydrates for each button press, after the user has pressed the button three times the configuration page 64 can indicate that a bolus of 1.5 units of insulin corresponding to, in this example, 15 grams of carbohydrates will be delivered. The conversion between carbohydrates and units of insulin can be based on known and/or stored carbohydrate ratios for the user. The user can cancel the quick bolus delivery at any time by selecting a cancel button 66.

Once the quick bolus has been programmed, either by the user indicating that the bolus programming is complete or by a predetermined period of time passing since the last button press, the pump notifies the user via, for example, audible and/or vibratory sounds that the bolus has been initiated. In some embodiments, a countdown notification 68 as shown in FIG. 4C can be shown on the user interface counting down to delivery of the bolus. Once the bolus delivery has been started, a notification 70 that the bolus has been started can also be presented on the user interface as shown in FIG. 4D.

The sounds or vibration notifying the user of the initiation of the bolus can also serve as a confirmation of the size of the bolus in some embodiments. This is convenient when a user is programming the bolus without looking at the user interface, such as when the user is discretely programming a bolus on a pump located under the user's clothing. For example, the pump can issue a series of vibrations, beeps or other sounds, with each sound corresponding to a predetermined increment of the quick bolus. A user therefore needs only to determine that the number of beeps and/or vibrations, etc., corresponds with the size of the bolus intended to be delivered, and then allow the pump to deliver the bolus without having to visually review the information presented on the GUI regarding the quick bolus. In some embodiments, the pump can also provide specific audible and/or vibratory feedback to indicate additional actions pertaining to programming of the quick bolus, such as, for example, two beeps and/or vibrations upon initiation of the quick bolus program, a beep and/or vibration as each increment is added to the quick bolus and one or more beeps and/or vibrations to indicate that the bolus delivery has been initiated. Further details regarding delivery of quick or audio boluses that can be delivered with pumps 12 of the present invention are disclosed in U.S. Pat. Nos. 8,287,495 and 8,346,399, which are hereby incorporated by reference herein. Alone or in combination with various ways to provide command input and/or receiving feedback regarding the quick bolus, natural language voice input from a user with, for example, natural language voice confirmation from the pump via a speaker, can be used in all of the embodiments described herein.

Figure 5:
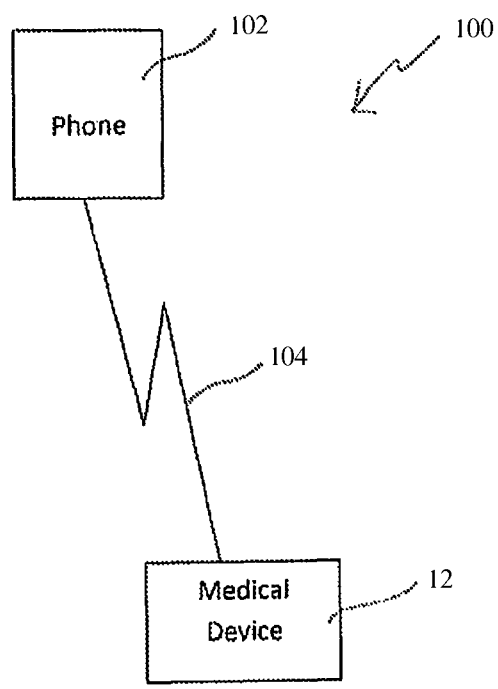
FIG. 5 is schematic representation of a system for facilitating programming of a medical device according to embodiments of the present invention.

Referring now to FIG. 5, a system 100 according to embodiments of the present invention includes a medical device such as an insulin pump 12 having a wireless connection 104 to a mobile phone 102, such as a smartphone, via, for example, Bluetooth®, Blue Tooth® low energy, mobile, Wi-Fi or other communications protocols and modalities. Although the system 100 is described with respect to a mobile phone, alternate types of remote consumer electronic devices could be used in place of a phone as the device 102, including, for example, an electronic tablet or a laptop or desktop computer. A remote consumer electronic device as used herein refers to devices having their own processor, memory, etc. that are useable for a variety of functions, such as, for example, phone calls, emails and accessing the internet, beyond simply being a remote control device for a medical device. In other embodiments of each of the systems and methods described throughout this disclosure, however, a remote device used with the present invention can be a dedicated remote control device. Similarly, although described with respect to an insulin pump, the medical device 12 can be any other type of programmable medical device capable of wirelessly communication with a mobile phone 12 or other device, including, for example, infusion pumps for infusing medicaments in addition to or other than insulin.

Figure 6:
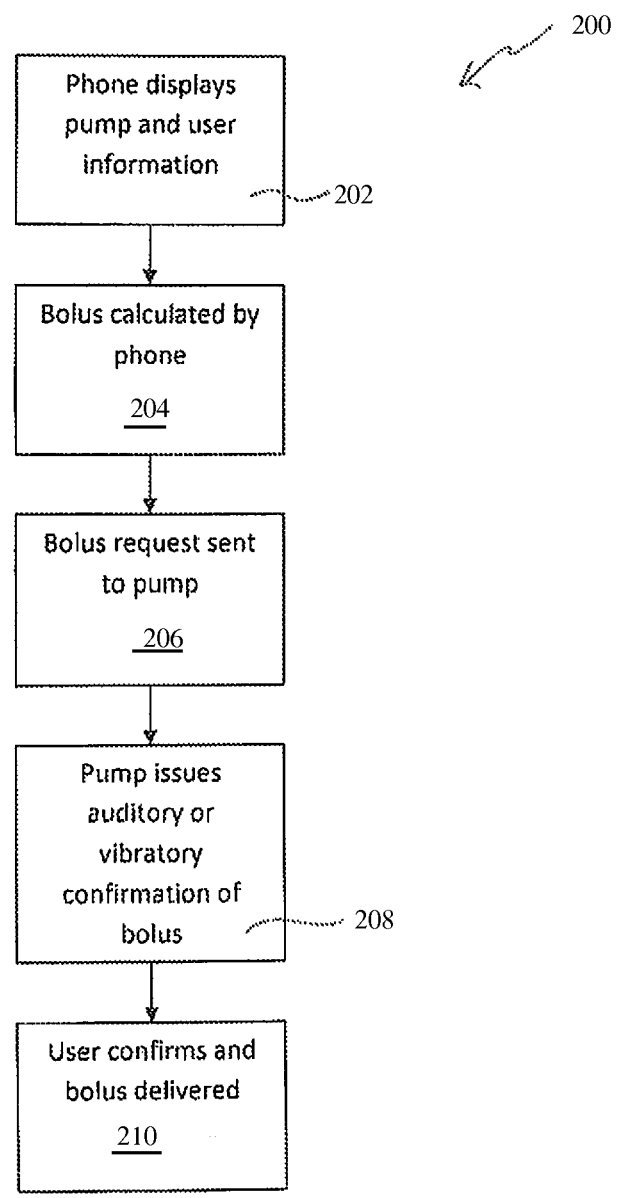
FIG. 6 is a flowchart of steps for using a mobile phone to aid in administering therapy with a medical device according to embodiments of the present invention.

In some embodiments, the smartphone 102 of the system of FIG. 5 can be used to program a bolus delivery by insulin pump 12, with notification and confirmation of the bolus provided by the pump in any manner similar to those of the quick bolus feature of the pump described above. Referring to FIG. 6, a method of initiating delivery of a bolus 200 with a mobile phone such as a smartphone begins with a smartphone that is wirelessly or otherwise operatively connected to an insulin pump displaying status items relating to the pump on the phone at step 202. When a bolus delivery is desired, the smartphone can calculate the bolus at step 204 taking into account parameters known through the pump such as, for example, insulin on board and blood glucose level as well as a number of carbohydrates the user is expected to consume. The bolus request is then sent from the smartphone to the pump at step 206 to initiate delivery of the bolus. After the pump receives the bolus request, the pump provides an auditory and/or vibratory notification relating to the bolus at step 208. For example, as with the quick bolus delivery methods described above, the pump can issue one beep and/or vibration for each predefined bolus increment to indicate a size of the bolus. At step 210, the pump delivers the bolus, either after a confirmation by the user or automatically after no user action during a predetermined period of time. In some embodiments, the confirmation is made by the user at the pump. In other embodiments, the user confirms delivery on the smartphone. In still other embodiments, the confirmation may be made on either the pump or the smartphone.

For example, if a user is going to eat a meal, the user can enter the number of carbohydrates that are going to be consumed into the smartphone and the phone can calculate a bolus based on the number of carbohydrates, insulin to carbohydrate ratio, insulin on board and current blood glucose level, for example. The calculated value, for example five units of insulin, is shown on the phone display or otherwise communicated to the user. The user can then execute a command on the phone to send the bolus to the pump. In some embodiments, the smartphone can have a software application thereon that facilitates the calculations and communicates with the pump. When the pump receives the command or other communication, the command from the smartphone causes it to provide confirmatory feedback as described herein, such as by playing an auditory and/or vibratory sequence representing the bolus, e.g., a series of five beeps representing each of the five units of insulin. If the auditory or vibratory sequence comports with the user's expectations, the user can confirm the delivery, such as by pressing a button on the pump, and the pump delivers the bolus as a result of the operating command from the smartphone. In other embodiments, the bolus can be automatically delivered a predetermined period of time after the sequence if the bolus is not cancelled. In some embodiments, feedback that can be the same as or different from that described above can also be provided at the smartphone or other device from which the bolus or other command is sent. In various embodiments, boluses can be calculated with the smartphone based on other parameters relating to treatment of a patient. For example, the smartphone could receive information relating to a blood glucose level of a patient, such as, for example, information from a continuous glucose monitor or blood glucose meter, and utilize that data to calculate a bolus.

In some embodiments, system 100 can be used to deliver extended boluses, e.g., boluses delivered slowly over a set extended period of time and split boluses, which are boluses in which a portion of the insulin is delivered immediately and a portion is delivered over an extended period. Further details regarding such boluses can be found in U.S. Pat. No. 6,852,104, which is hereby incorporated by reference in its entirety. In such embodiments, an extended bolus or an extended portion of a bolus can have a different auditory and/or vibratory indicator, such as, for example, a different tone, different key, different harmonic, different sound length, etc. than boluses or portions of boluses that are delivered as fast as possible. For example, if a bolus is programmed with the smartphone and sent to the pump that includes delivering two units of insulin immediately and three units of insulin over the next hour, the pump can issue two identical sounds or vibrations representing the two units of insulin to be delivered immediately followed by three identical sounds or vibrations that are different from the first two sounds or vibrations, with the final three sounds or vibrations representing the three units of insulin to be delivered over the extended period. In some embodiments, the pump can also use sounds or vibrations to indicate the amount of time over which an extended bolus or portion of a bolus is delivered. For example, additional sounds or vibrations can be issued with each indicating a predetermined increment of time, such as a half hour, or extended boluses delivered over different periods of time can each be indicated with distinct size increment sounds. Visual and/or natural language indications as described herein may also be used alone or in combination with sound and/or vibratory feedback techniques for delivery of extended and split boluses.

Figure 7:
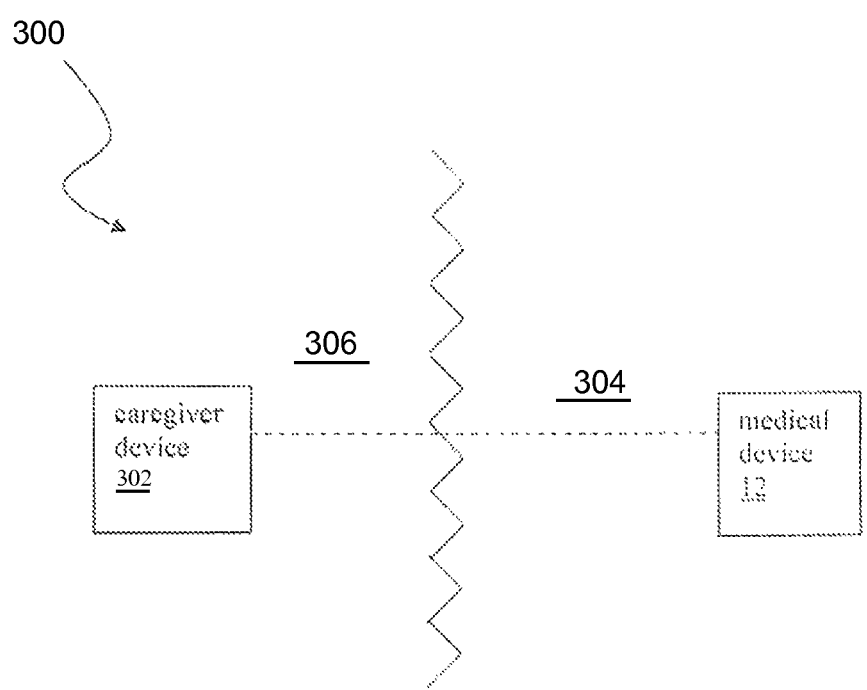
FIG. 7 is schematic representation of a system for remotely authorizing delivery of a medicament according to embodiments of the present invention.

Referring now to FIG. 7, a schematic representation of a system 300 for remote authorization of delivery of a medicament is depicted. System 300 includes a medical device, such as, for example, an insulin pump in a first location 304. System 300 also includes a caregiver device 302. Typically, caregiver device 302 will be in a location 306 remote from the location 304 of the medical device 12. A location 306 remote from the location 304 of the medical device 12 could include, for example, anywhere between a place hundreds of miles from the medical device to a location in the same room as the medical device 12. Communication between caregiver device 302 and medical device 12 therefore may be performed done wirelessly via, for example, Bluetooth®, Bluetooth® low energy, mobile, Wi-Fi or other communications protocols and modalities. In some embodiments, caregiver device 302 is a mobile phone, such as smartphone. Alternatively, caregiver device 302 can be any other type of device capable of wired or wireless communication with medical device 12 such as, for example, an electronic tablet or a laptop or desktop computer.

Figure 8:
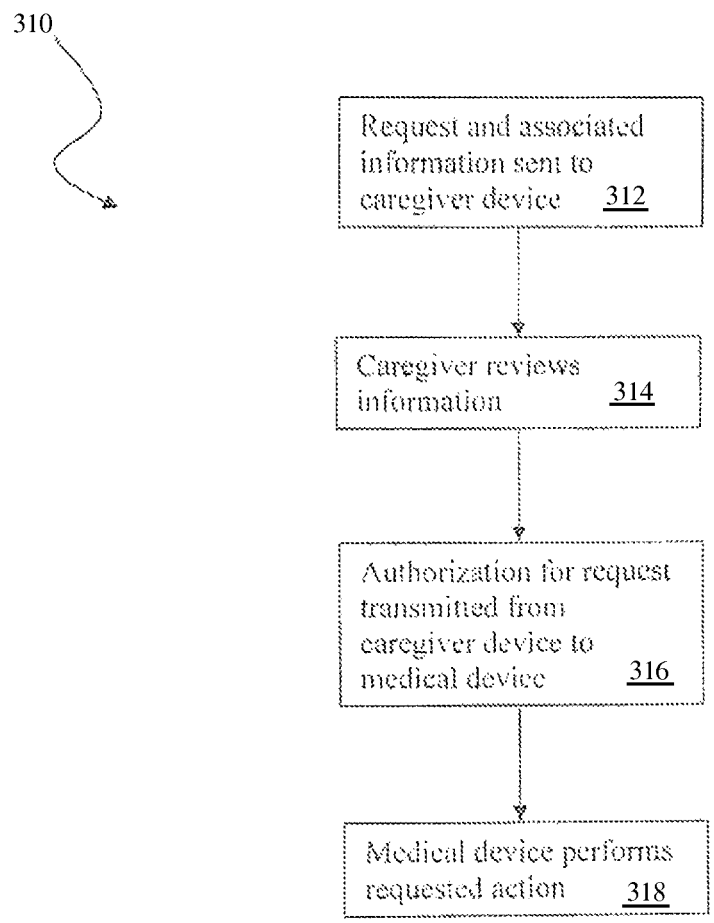
FIG. 8 is a flowchart of a method of remotely authorizing delivery of a medicament according to embodiments of the present invention.

FIG. 8 depicts a flowchart of a method 310 of remotely authorizing delivery of a medicament according to an embodiment of the present invention. At step 312, the medical device sends a request through a wireless connection to the caregiver device. The request can include details pertaining to deliver of a medicament with the medical device, such as a number of units of insulin requested for a bolus. The request can also include additional information to aid the caregiver in determining whether the request is appropriate. In the case of an insulin bolus, for example, the request can include a current or recent blood glucose level, a number of carbohydrates and/or other nutritional information pertaining to a meal about to be or recently consumed and/or the amount of unmetabolized insulin left in the patient's system, or insulin on board (IOB). In one embodiment, the information can include a picture of a meal about to be consumed by the patient for review by a parent or caregiver overseeing a child patient that may have difficulty counting the carbohydrates in a meal. In some embodiments, the request can be entered into a user interface of the medical device by the patient. Alternatively, the medical device can automatically determine that an operation should be carried out based on available data such as, for example, blood glucose level of the patient. In such an embodiment, the request can be automatically transmitted to the caregiver device or an alert can appear on the user interface requiring patient confirmation to transmit the request. At step 314, the request and associated information can be displayed on the caregiver device for review by the caregiver.

If the caregiver determines after review of the request and associated information that the requested operation should be carried out, the caregiver provides authorization through the caregiver device that is transmitted wireless to the remotely located medical device at step 316. An alert can appear on a user interface of the medical pump that the request has been authorized. In some embodiments, the patient can be required to confirm the request to initiate the operation. Alternatively, the operation can be automatically carried out after being authorized by the caregiver. After receiving final authorization from the caregiver device and/or through its own user interface, the medical device carries out the requested operation at step 318. If the caregiver determines that the requested operation should not be carried out, the caregiver can cancel the request. In some embodiments, a canceled request communication is then transmitted to the medical device and displayed on the user interface of the device.

In some embodiments, a local override feature can be incorporated into the system. If the medical device is unable to establish a connection with the caregiver device due to, for example, connections problems, the request can be authorized locally by an authorized individual. For example, for a child at school the school nurse could enter a password or otherwise authenticate authority to locally authorize the delivery. In certain embodiments, the local override feature can also be employed when the caregiver device is connected to but does not respond by either authorizing or cancelling the request within a predetermined period of time.

In some embodiments, medical device 12 and/or caregiver device 302 can communicate with and receive data from one or more other devices or sensors, such as, for example, a blood glucose meter or continuous glucose monitor. In certain embodiments, the medical device can receive data from the additional device and transmit the data to the caregiver device along with the request and other corresponding information. Alternatively, the caregiver device can communicate directly with the other device to receive data from the device.

In some embodiments, the caregiver device 302 can include software, such as an application running on a smartphone, that can take into account data received from the medical device 12 and/or other devices, such as, for example, blood glucose level, insulin on board, and carbohydrates to be consumed, to determine whether an operation should be performed with the medical device, such as a bolus delivery, and make any necessary calculations for such operations. In such embodiments, if the caregiver device 302 determines that an operation such as a bolus delivery should be performed, the caregiver device can wirelessly transmit a command to the medical device 12 to carry out the operation. In some embodiments, the medical device can automatically carry out the operation. Alternatively, an alert can appear on a user interface of the medical device requiring a confirmation from the patient to carry out the operation.

Figure 9:
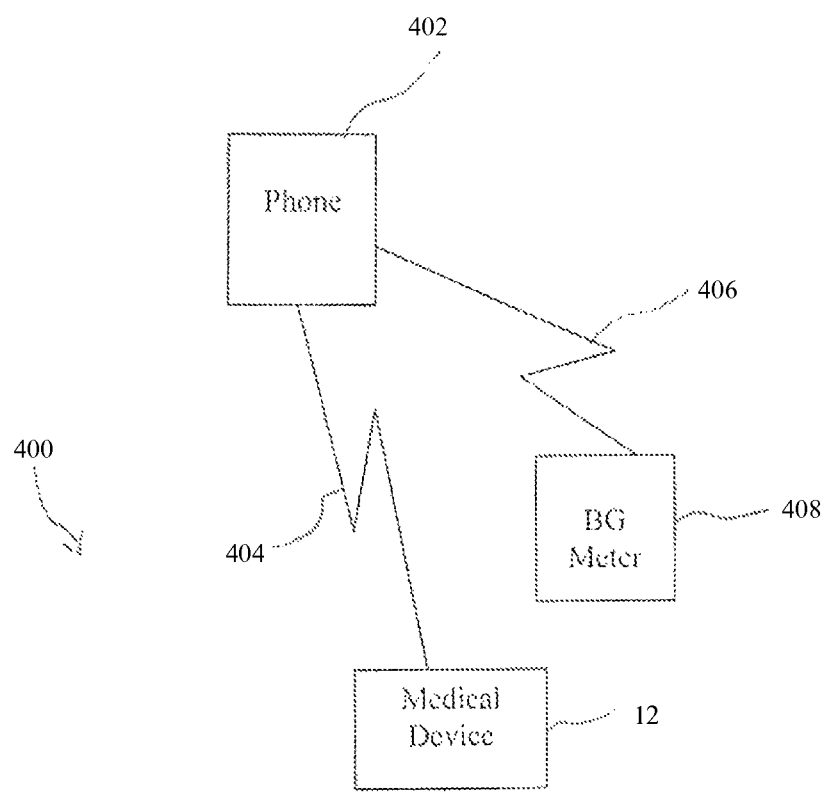
FIG. 9 is schematic representation of a system for facilitating programming of a medical device according to embodiments of the present invention.

Referring now to FIG. 9, a system 400 according to embodiments of the present invention includes a medical device such as an insulin pump 12 having a wireless connection 404 to a mobile phone 402 or other remote consumer electronic device, such as a smartphone, via, for example, Bluetooth®, Bluetooth® low energy, mobile, Wi-Fi or other communications protocols or modalities. In some embodiments, the phone 402 can also have a wireless or wired connection 406 with a blood glucose meter 408 or continuous glucose monitor (CGM) for receiving data from the blood glucose meter 408 or CGM. Although the system 400 is described with respect to a mobile phone, alternate types of remote consumer electronic devices could be used in place of a phone as the device 402, including, for example, an electronic tablet or a laptop or desktop computer. Similarly, although described with respect to an insulin pump, the medical device 12 can be any other type of programmable medical device capable of wirelessly communication with a mobile phone 402 or other device, including, for example, infusion pumps for infusing medicaments other than insulin.

Figure 10:
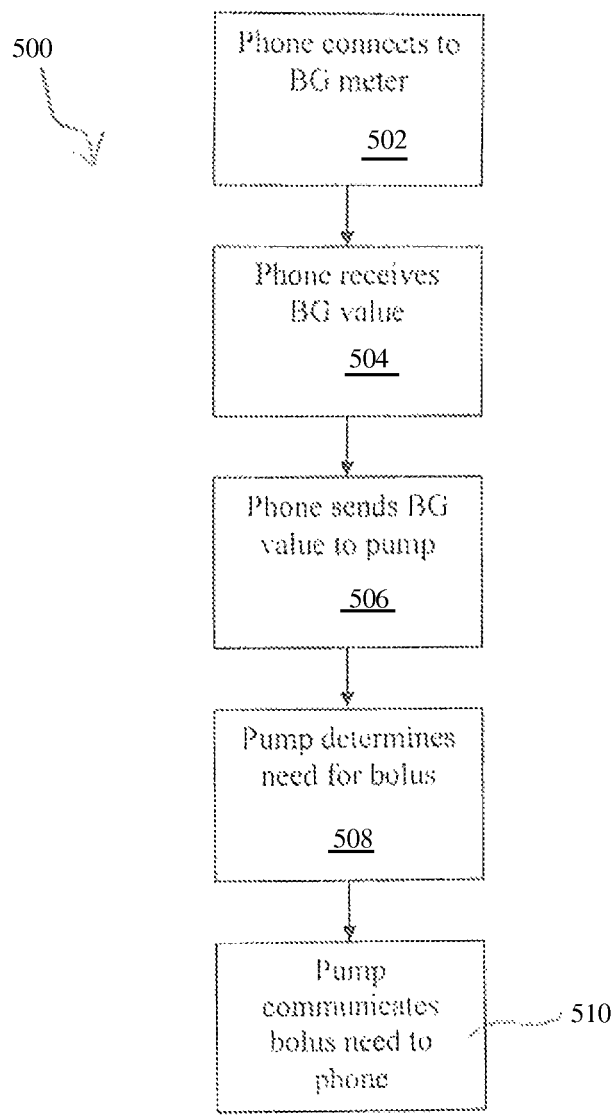
FIG. 10 is a flowchart of steps for using a mobile phone to aid in administering therapy with a medical device according to embodiments of the present invention.

FIG. 10 depicts a flowchart of an operation sequence for using the system 400 of FIG. 9 to aid in administering therapy with the insulin pump 12. At step 502, the phone 402 establishes a connection 406 with the blood glucose meter 408 or CGM. The phone 402 receives data from the blood glucose meter 408 or CGM such as a current or recent blood glucose value from a blood glucose meter 408 at step 504. The blood glucose value is then transmitted at step 506 to the infusion pump 12. The infusion pump 12 analyzes the data at step 508 as if the blood glucose value was entered in the pump's user interface or received directly from the blood glucose meter to determine if a bolus is needed. Generally, and as discussed in more detail in applications incorporated by reference herein, this calculation takes into account at least the blood glucose value, a target blood glucose value or range, and any insulin remaining in the user's system that will subsequently affect the user's blood glucose level, or insulin on board (IOB).

The correction bolus determination is communicated from the insulin pump 12 to the phone 402 at step 510. Depending on the determination made by the pump 12, the communication could include, for example, a general recommendation to take a correction bolus, a recommendation to take a correction bolus of a specific amount calculated by the pump, or a recommendation to recheck blood glucose level after a period of time due to IOB. If the recommendation is to take a correction bolus, the communication can refer the patient to the pump to deliver and/or calculate the bolus amount. Alternatively, the phone 402 can include software to make the determination regarding whether or not a bolus is needed and, if so, calculate a specific amount for a correction bolus, provided that the phone has received the necessary information for such a calculation either from the pump or through the phone user interface, such as IOB and a correction factor. In such an embodiment, the phone 402 could then transmit that amount to the pump 12. When the user refers to the pump, the blood glucose information and/or the recommended bolus can be displayed. The bolus can then easily be delivered.

In some embodiments, a phone 402 can be used to aid in insulin pump therapy without having a connection to a blood glucose meter. In such embodiments, the phone 402 could receive from the pump 12 and optionally display on the phone 12 any relevant variable from the pump, such as IOB. Other information relevant to pump operation, such as battery life and insulin remaining in the pump could also be stored and/or displayed on the phone 12. The phone could also display predicted future blood glucose level(s) from a previously known blood glucose level either entered into the phone or received from the pump. Such predicted future blood glucose levels could be determined based on, for example, blood glucose/CGM trends, IOB and food/carbohydrates recently consumed. In general, any information that can be displayed on the pump 12 may be displayed on the phone 102 in any desired format or quantity. For instance, the phone 402 display can simply "mirror" that information displayed or capable of being displayed on the pump 12 in exactly or substantially the same manner. Alternatively, any subset of data that is otherwise displayed or capable of being displayed on pump 12 may be displayed on the phone 402 as desired.

In certain embodiments, a phone 402 having a connection with a blood glucose meter can also provide therapy assistance for manual delivery of insulin or other medicament, such as, e.g., glucagon, rather than treatment with an insulin pump. For instance, the phone can utilize values received from the blood glucose meter to calculate, e.g., insulin bolus amounts for delivery with a non-connected device such as a syringe. In such embodiments, the phone 402 can receive insulin dose and carbohydrate consumed values entered by the user and use those values in calculating the recommended dose.

Figure 11:
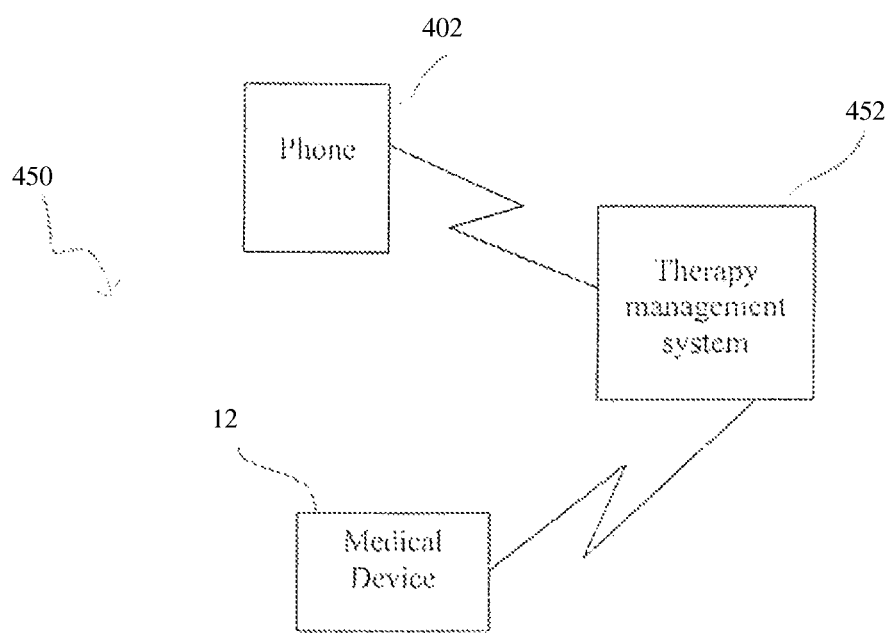
FIG. 11 is a schematic representation of a system for using a mobile phone to facilitate data logging of use of a medical device according to embodiments of the present invention.

A mobile phone such as a smartphone can also aid in logging and reviewing data associated with treatment using an insulin pump. One embodiment of a system 450 employing such an approach is shown in FIG. 11. The system can include a mobile phone 402 such as a smartphone and a medical device 12 such as an insulin pump that are each capable of communicating with a therapy management system 452 through a wireless or wired connection. Therapy management system 452 can operate on any device having memory for storing therapy parameters and a processor for executing commands, including, for example, a laptop or desktop computer, an electronic tablet or a mobile phone such as a smartphone. In one embodiment, the therapy management system 452 can be operated on the same smartphone 402 used to capture data. Where the therapy management system 452 is operated on a separate device from the phone 402, the medical device 12 can, but need not be, capable of communication with the phone 402.

Advanced features of the smartphone 402 or other device can be used to obtain more detailed logging of meals for the therapy management system than simply a number of carbohydrates consumed as would be entered into a pump or a therapy management system running on a computer independently of a connection to the smartphone or other device. In one embodiment, a user can take a picture of a meal that is about to be consumed with the camera of the phone or, e.g., tablet computer. In another embodiment, the speaker of the phone or tablet computer can be employed by the user to take voice notes on a meal or other event such as exercise.

The picture, voice message, or other data can be downloaded from the phone 402 or tablet computer, etc. to the therapy management system 452 through either a wireless or wired connection. In some embodiments, the data is automatically analyzed for its content, such as by image recognition software or voice recognition software and the user is present with data, such as number of carbohydrates and other nutritional information, that correlates to the downloaded picture, voice message, or other data, for storage in the therapy management system. In one embodiment, software utilized by the therapy management system undertakes this analysis. Alternatively, application software utilized by the smartphone (software resident on the smartphone and/or on a remote computing device such as a server) can undertake the analysis prior to transmitting to the therapy management system 452. In such embodiments, the therapy management system and/or the smartphone can include access to a nutritional lookup database that includes carbohydrates and other nutritional information for various foods. In other embodiments, the data can be transmitted to the therapy system as an image, voice, etc. file for later manual review and manual entry of corresponding nutritional data. Each data file acquired with the smartphone can have a time stamp that is also transmitted to the therapy management system to identify a time and date when it was acquired. In some embodiments, the picture can be analyzed by a caregiver, such as a parent, either manually or utilizing a computer system for automatic analysis, and the caregiver can then remotely authorize delivery of a bolus or other action or actions as may be appropriate.

The therapy management system 452 can also be connected with the pump 12 and therefore can also track operations carried out by the pump, such as delivery of boluses. In some embodiments, the therapy management system also receives blood glucose values, either from the medical device or smartphone or through a separate connection to a blood glucose meter. The therapy management system can therefore match meals consumed, pump operations, and/or blood glucose levels by the time stamps associated with those events. The system therefore permits a user or caregiver to retrospectively go back and look at previous therapy decisions that were made and the subsequent effects in order to provide a guide for future therapy decisions.

Although generally described herein with respect to delivery of a medicament by a medical device, it should be understood that embodiments of systems and methods described herein can be utilized with any type of operation that can be performed by a medical device. In addition, although generally described herein with respect to an infusion pump, and specifically an insulin pump, it should be understood that the system and method can be employed with any type of medical device capable of wireless communication with a smartphone, such as, for example, infusion pumps for delivering medicaments other than insulin. In addition, although primarily described with respect to wireless communications, various embodiments in which communications between the pump and caregiver device are facilitated through wired connections are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230; 2013/0053816; 2013/0159456; and 2013/0306191 commonly owned U.S. patent application Ser. Nos. 13/800,387; 13/800,453; 13/800,595; 13/801,230; 13/801,274; 13/827,383; 13/827,707; 13/828,958; 13/829,115; 13/832,531; 13/832,841; 13/837,661; 13/837,777; 13/838,084; 13/838,617; 13/841,028; 13/841,432; 13/842,005; 13/842,990 and 13/923,556; and commonly owned U.S. Provisional Application Serial Nos. 61/874,428 and 61/875,979.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of delivering a medicament bolus with a medical infusion pump, comprising:
   determining a medicament bolus delivery for a medical infusion pump with a software application operating on a remote consumer electronic device;
   transmitting an operating command for delivery of the bolus from the remote consumer electronic device to the medical infusion pump via the software application operating on the remote consumer electronic device:
   causing an indication of the bolus to issue from the medical infusion pump, the indication of the bolus comprising a series of increment indications including at least one of an auditory indication or a vibratory indication, the series of increment indications representing a size of the bolus with each auditory or vibratory indication corresponding to a predetermined increment; and causing the medical infusion pump to deliver the bolus to a patient.

2. The method of claim 1, wherein causing the medical infusion pump to deliver the bolus to a patient includes receiving a confirmation of the bolus following issuing an indication of the bolus.

3. The method of claim 2, wherein the confirmation is received via the remote consumer electronic device.

4. The method of claim 2, wherein the confirmation is received via the medical infusion pump.

5. The method of claim 1, wherein causing the medical infusion pump to deliver the bolus to a patient includes delivering the bolus a predetermined period of time after issuing the indication of the bolus.

6. The method of claim 1, further comprising displaying status items relating to the medical infusion pump on a user interface of the remote consumer electronic device.

7. The method of claim 1, wherein determining a bolus delivery for a medical infusion pump includes utilizing the software application operating on the remote consumer electronic device to calculate the size of the bolus.

8. The method of claim 7, wherein the remote consumer electronic device calculates the size of the bolus based at least in part on information entered through a user interface of the remote consumer electronic device.

9. The method of claim 8, wherein the information includes a number of carbohydrates to be ingested.

10. The method of claim 1, wherein the remote consumer electronic device is a mobile phone.

11. The method of claim 1, wherein the remote consumer electronic device is a tablet computer.

12. A method of programming a medical infusion pump, comprising:
    determining with a software application operating on a remote consumer electronic device an amount of a medicament bolus for delivery by a medical infusion pump;
    transmitting an operating command for delivery of the bolus amount from the remote consumer electronic device to the medical infusion pump via the software application operating on the remote consumer electronic device;

causing an indication of the bolus amount to issue from the medical infusion pump, the indication of the bolus amount comprising a series of increment indications including at least one of an auditory indication or a vibratory indication, with each auditory or vibratory indication corresponding to a predetermined increment of the bolus amount.

13. The method of claim 12, further comprising displaying status items relating to the medical infusion pump on a user interface of the remote consumer electronic device.

14. The method of claim 12, wherein determining an amount of a medicament bolus for delivery by a medical infusion pump includes utilizing software application operating on the remote consumer electronic device to calculate the bolus amount.

15. The method of claim 14, wherein the remote consumer electronic device calculates the bolus amount based at least in part on information entered through a user interface of the remote consumer electronic device.

16. The method of claim 15, wherein the information includes a number of carbohydrates to be ingested.

17. The method of claim 12, wherein the remote consumer electronic device is a mobile phone.

18. The method of claim 12, wherein the remote consumer electronic device is a tablet computer.

19. A method of delivering a medicament bolus with a medical infusion pump, comprising:

receiving at a remote consumer electronic device, via a software application operating on the remote consumer electronic device, a request to deliver a medicament bolus with a medical infusion pump;

presenting on a user interface of the software application operating on the remote consumer electronic device information pertaining to the requested bolus;

receiving through the user interface of the software application operating on the remote consumer electronic device an authorization to proceed with delivery of the medicament bolus;

transmitting from the remote consumer electronic device to the medical infusion pump the authorization to proceed with delivery of the medicament bolus via the software application operating on the remote consumer electronic device; and causing the medical infusion pump to deliver the bolus to a patient following receipt of the authorization from the remote consumer electronic device.

20. The method of claim 19, wherein presenting on a user interface of the remote consumer electronic device information pertaining to the requested bolus includes presenting patient-specific information of the patient on the user interface.

* * * * *